United States Patent [19]
Cornu et al.

[11] Patent Number: 5,177,779
[45] Date of Patent: Jan. 5, 1993

[54] NON-DESTRUCTIVE RADIATION INSPECTION APPARATUS INCLUDING A SIGHTING UNIT

[75] Inventors: Michael L. P. Cornu, Montereau; Claude J. Krempel, Vaux Le Penil, both of France

[73] Assignee: Societe Nationale D'Etude et de Construction de Moteurs D'Aviation "S.N.E.C.M.A.", Paris, France

[21] Appl. No.: 731,325

[22] Filed: Jul. 17, 1991

[30] Foreign Application Priority Data

Jul. 18, 1990 [FR] France .................. 90 09141

[51] Int. Cl.⁵ .................................. A61B 6/08
[52] U.S. Cl. .................................. 378/206; 378/63; 378/58; 378/205
[58] Field of Search .............. 378/58-60, 378/62-63, 204, 205, 206

[56] References Cited

U.S. PATENT DOCUMENTS

| | | | |
|---|---|---|---|
| 3,628,021 | 12/1971 | MacDonald | 378/206 |
| 4,078,180 | 3/1978 | Green | 378/59 |
| 4,283,628 | 8/1981 | Kulekor et al. | 378/60 |
| 4,337,502 | 6/1982 | Lescrenier | 378/206 |
| 4,502,147 | 2/1985 | Michaels | 378/206 |
| 4,521,905 | 6/1985 | Hosokawa . | |
| 4,969,177 | 11/1990 | Otsuki et al. | 378/206 |

FOREIGN PATENT DOCUMENTS

| | | | |
|---|---|---|---|
| 1922861 | 11/1970 | Fed. Rep. of Germany | 378/60 |
| 0075948 | 3/1989 | Japan | 378/60 |
| 2109660 | 6/1983 | United Kingdom . | |

OTHER PUBLICATIONS

Mechanical Engineering, vol. 106, No. 2, Feb. 1984, pp. 34-37, J. Fagenbaum, "NDE: Its Role in Nuclear Power".

Primary Examiner—David P. Porta
Attorney, Agent, or Firm—Oblon, Spivak, McClelland, Maier & Neustadt

[57] ABSTRACT

Apparatus for inspecting a part by means of X or gamma radiation comprises an arm carrying an X or gamma ray emitter, and a remote light ray emitter for emitting a ray of light parallel to the arm. An oblique mirror which is transparent to the radiation is mounted on the arm in the path of the radiation beam to reflect the ray of light in a direction parallel to the radiation beam and towards the part to be inspected. In this manner identification of the part to be inspected can be achieved by means of a camera carried obliquely on the arm, without having to mount the bulky light emitter close to the components which are essential for carrying out the inspection. The apparatus is particularly useful for checking weldings in narrow bores.

3 Claims, 2 Drawing Sheets

NON-DESTRUCTIVE RADIATION INSPECTION APPARATUS INCLUDING A SIGHTING UNIT

BACKGROUND OF THE INVENTION

1. Field of the invention

The present invention relates to apparatus for the non-destructive inspection of parts by irradiation, for example using X or gamma radiation, which includes a sighting unit.

2. Summary of the prior art

Such apparatus essentially comprises a unit for emitting the radiation towards the part to be inspected, and means for taking an image of the part, such as a photographic film. In order to locate easily the direction of the radiation beam and to check that the image obtained does relate to the irradiated area of the part, the apparatus is frequently provided with a sighting unit comprising means for emitting a ray of light which is temporarily included in the radiation beam and which supplies a reference point for observation through its interference with the part. However, the problem with this is that the light ray emitter is cumbersome, and its presence impedes the transmission of the checking radiation.

It is necessary therefore to resort to removing the light ray emitter after the stage of setting the sighting on the area of the part to be checked, which is hardly possible if the apparatus has been inserted inside certain parts such as small diameter bores. Moreover, the light ray emitter can prevent the introduction of the apparatus into such bores.

SUMMARY OF THE INVENTION

It is an object of the invention to obviate these drawbacks, and to this end there is provided apparatus for inspecting a part by means of X or gamma radiation, comprising an X or gamma radiation emitter, an arm carrying said radiation emitter, said arm having a longitudinal axis and said radiation emitter being arranged to emit said radiation as a beam along a path substantially perpendicular to said longitudinal axis, a light ray emitter remote from said radiation emitter, said light ray emitter comprising a light source, an optical fibre for transmitting light from said source, and a terminal mounted on said arm for receiving light from said optical fibre and emitting a ray of light along said arm, a light reflecting mirror disposed in said path of said radiation beam, said mirror being transparent to said radiation and being arranged to receive said light ray emitted from said terminal and to reflect said ray in the direction of said beam towards said part to be inspected, first means for taking an image of the part through which said radiation passes, and second means for taking an image of the part sighted by said light ray.

With this arrangement the light ray emitter is located remote from the monitoring radiation beam, although the light ray itself is transmitted within the beam and preferably on the axis of the latter. There is therefore no need to remove the light ray emitter, and the light ray is available at the time the images are taken. In addition, very high accuracy of the position of the light ray can be achieved. Finally, the apparatus can be used without difficulty for inspection or checking within very small volumes.

Preferably, the second image taking means comprises a camera which is carried tangentially by the arm in the transverse plane containing the radiation beam, and which is able to be aimed at the area of the part on which the light ray is incident.

A greater flexibility of utilization is afforded if the mirror is fixed on a plate which is mounted in a removable manner on the arm, possibly by means of fixing screws passing through arcuate holes which are provided in the plate and which permit adjustment of the angular 1 position of the mirror. Indeed, it is then possible to replace the mirror temporarily by an aiming device for the light ray or by an arm horizontality detector.

DESCRIPTION OF THE PREFERRED EMBODIMENT

Figure 1:
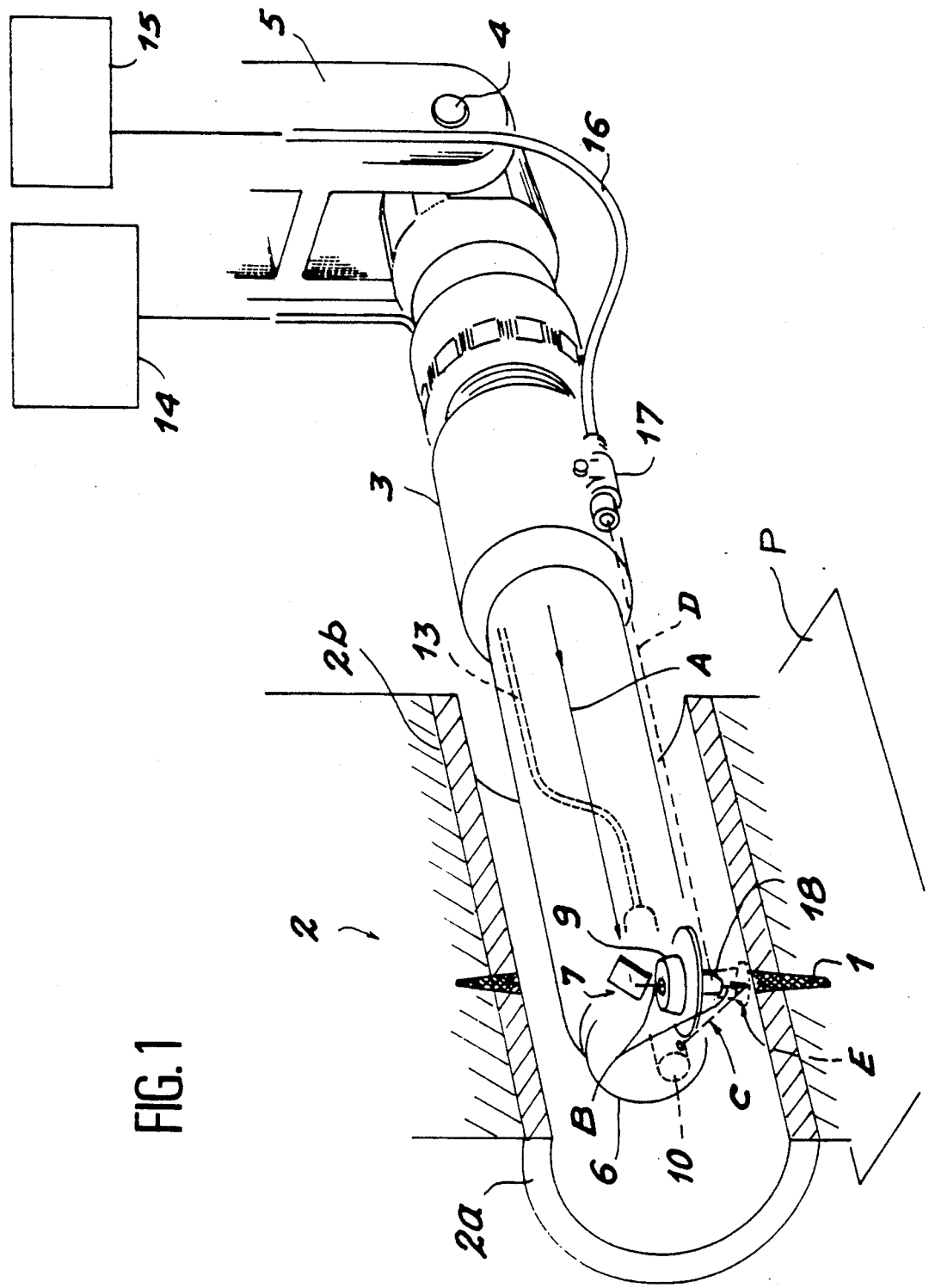
FIG. 1 is a diagrammatic view showing one embodiment of the apparatus in accordance with the invention during operation.

The part to be inspected may, for example, be a circular weld between two cylindrical elements 2a and 2b of a tube 2 of small diameter. The inspection apparatus comprises a tubular arm 3 which is hinged at one end 4 on a support 5 and which has its free other end 6 inserted into the tube 2 in front of the weld 1. The free end 6 contains an X-ray emitter 7, which in this example is an anticathode inclined at 45° to the longitudinal axis of the arm 3 along which an electron beam is projected. A conical beam E of X-rays is therefore emitted around an emission axis B extending perpendicularly to the axis of the arm and in a radial direction within the tube 2. A lead truncated cone 9 fitted with a filter is arranged around the transmission axis B inside the arm 3 so as to focus the emitted radiation beam towards the weld 1. A photographic film or plate P is arranged outside the tube 2 to obtain an X-ray negative of the area inspected.

To check the correct positioning of the radiation beam relative to the area of the part to be inspected, a camera 10 is fixed outside the arm 3 for taking monitoring images along a sighting direction C extending obliquely relative to the emission axis B towards the irradiated part of the weld 1. A transmission cable 13 extends from the camera 10 along the tube 3 and the support 5, and enables the images taken by the camera 10 to be viewed on a screen 14.

A laser 15 is provided as a source of light which travels along an optical fibre 16 to an emitter terminal 17 which emits a light ray D. Suitable terminals 17 are available in the trade, and it is envisaged utilizing the one sold under reference NZ 44 FO1 yy the A2J Company (Fontenay sous Bois, France).

Figure 2:
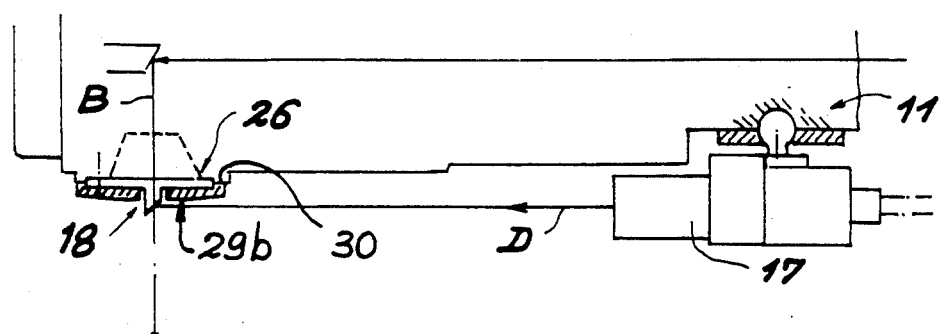
FIG. 2 is a diagram illustrating the principles of the apparatus.

The terminal 17 is attached to the arm 3 by means of a coupling comprising a ball joint or a plate 11 which includes rotational and swivel adjustment means, thus permitting adjustment of the direction of the emitted light ray D (FIG. 2). The terminal 17 is remote from the free end 6 of the arm 3 and remains outside the tube 2. Therefore it does not prevent or hinder the introduction of the arm 3 into the tube. The axis of the light ray D extends along the arm 3 and intersects the radiation beam E. Within the beam E the light ray D is intercepted by a mirror 18 inclined at 45° to deflect the light ray through a right angle so that it is then directed along the axis B of the beam E towards the weld 1. The light ray D therefore enables rapid detection of the position of the beam E, and in particular of the area which is to be inspected by the irradiation.

Figure 3:
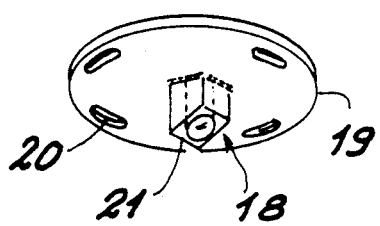
FIG. 3 is a perspective view of the mirror which is used in the apparatus of FIG. 1.

It will be seen in FIG. 3 that the mirror 1B is fixed on a plate 19 which may be removably mounted on the arm 3. For this purpose the plate 19 is provided with four arcuate holes 20 arranged around the mirror 18 for the passage of screws for fixing the plate to the arm 3. The arcuate shape of the holes permits adjustment of the angular position of the mirror 18 around the emission axis B, and hence enables the mirror to be correctly oriented for reflecting the light ray a desired.

The plate 19 and the body of the mirror 18 are made of Plexiglas, and the reflecting part of the mirror 18 is formed by a silver coating. This assembly is practically transparent to X-rays and therefore does not hinder the inspection of the part.

Figure 4:
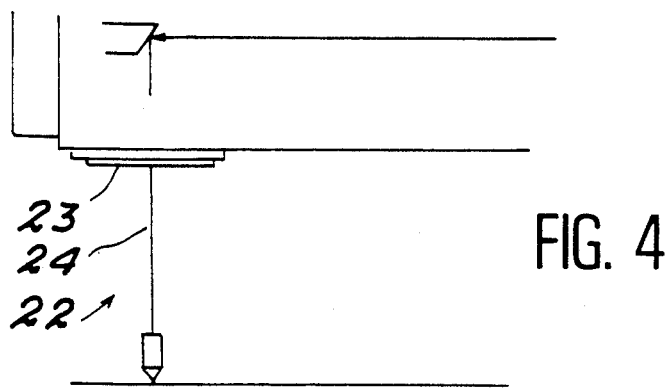
FIGS. 4 and 5 are diagrams respectively illustrating arrangements for checking the horizontality of the arm of the apparatus and for checking the aiming of the light ray emitter.

The removable mirror 18 provides certain advantages, although it is not removed when sighting. For example, it may be replaced, for the purpose of a preliminary stage shown in FIG. 4 in which the position of the arm 3 is adjusted, by a horizontality detector 22 consisting of a perforated plate 23 which can be screwed to the arm in place of the plate 19 of the mirror 18 and which carries a plumb line 24. The angular position of the arm 3 is adjusted by examining the position of the plumb line 24 relative to a calibration diagram.

Figure 5:
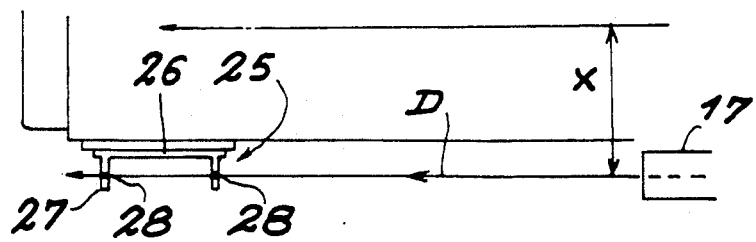

The mirror 18 may also be replaced by an aiming device 25 as shown in FIG. 5, the device consisting of a plate 26 which can be fixed to the arm 3 in place of the plate 19 or the plate 23 and which carries two parallel targets 27 each provided with a hole 28, the holes 28 being in alignment. With the device 25 in place, the mounting 11 of the terminal 17 is adjusted until the emitted light ray D passes through the two holes 28. When this has been achieved, the terminal 17 is fastened in position and the mirror 18 is refitted in place of the aiming device 25.

Figure 6A:
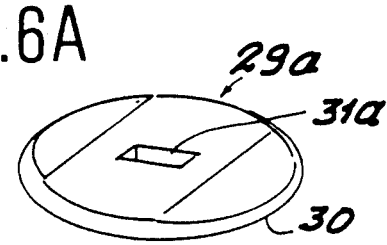
FIGS. 6a and 6b show alternative aperture or window devices for shaping the radiation beam.
Figure 6B:
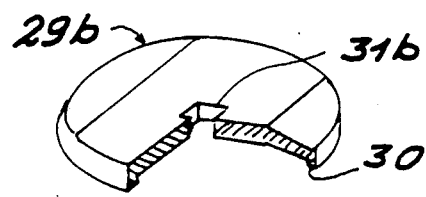

To improve the X-ray inspection, windows 29a or 29b for focussing X or gamma rays (FIGS. 6A and 6B) can be fitted in the apparatus. In the embodiment shown the consist of discs having a collar 30 on one of their faces to enable the window 29a or 29b to be fitted around the plate 19. An opening 31a or 31b in the disc sets the aperture of the beam E, and the mirror 18 protrudes through the opening 31a or 31b as shown in FIG. 2 so that the path of the light ray is not impeded.

The opening 31a or 31b is selected to suit the taking of a succession of images which constitute what is termed a dynamic inspection of a part. In the example shown, the tube 2 is rotated around its axis in equal angular steps and an image is taken at each step. The judicious selection of the window 29a, 29b enables images to be obtained of successive portions of the circular weld 1 without overlaps.

The advantage of the laser sighting unit in accordance with the invention is its small overall size, which permits utilization of the arm inside small diameter holes without removing the sighting unit, while avoiding parallax errors between the laser sighting beam and the X-ray inspection beam, since the axes of the two beams remain permanently coincident.

What is claimed is:

1. An apparatus for inspecting a part by means of X or gamma radiation, comprising:
   an X or gamma radiation emitter,
   an arm carrying said radiation emitter, said arm having a longitudinal axis and said radiation emitter being arranged to emit said radiation as a beam along a path substantially perpendicular to said longitudinal axis,
   a light ray emitter remote from said radiation emitter, said light ray emitter comprising
      a light source,
      an optical fiber for transmitting light from said source, and
      a terminal mounted on said arm for receiving light from said optical fiber and emitting a ray of light along said arm,
   a light reflecting mirror disposed in said path of said radiation beam, said mirror being transparent to said radiation and being arranged to receive said light ray emitted from said terminal and to reflect said ray in the direction of said beam toward said part to be inspected,
   first means for taking an image of the part through which said radiation passes,
   second means for taking an image of the part sighted by said light ray, and
   wherein said mirror is fixed on a plate, said plate being removably mounted on said arm, and provided with arcuate holes, said plate being mounted on said arm by fixing screws passing through said holes, wherein said arcuate holes permit adjustment of the angular position of said mirror.

2. An apparatus for inspecting a part by means of X or gamma radiation, comprising:
   an X or gamma radiation emitter,
   an arm carrying said radiation emitter, said arm having a longitudinal axis and said radiation emitter being arranged to emit said radiation as a beam along a path substantially perpendicular to said longitudinal axis,
   a light ray emitter remote from said radiation emitter, said light ray emitter comprising
      a light source,
      an optical fiber for transmitting light from said source, and
      a terminal mounted on said arm for receiving light from said optical fiber and emitting a ray of light along said arm,
   a light reflecting mirror disposed in said path of said radiation beam, said mirror being transparent to said radiation and being arranged to receive said light ray emitted from said terminal and to reflect said ray in the direction of said beam toward said part to be inspected,
   first means for taking an image of the part through which said radiation passes,
   second means for taking an image of the part sighted by said light ray, and wherein said light ray emitting terminal is mounted on said arm by means permitting positional adjustment of said terminal by rotation and swiveling thereof.

3. An apparatus for inspecting a part by means of X or gamma radiation, comprising:
   an X or gamma radiation emitter,
   an arm carrying said radiation emitter, said arm having a longitudinal axis and said radiation emitter being arranged to emit said radiation as a beam along a path substantially perpendicular to said longitudinal axis, a light ray emitter remote from said radiation emitter, said light ray emitter comprising a light source, an optical fiber for transmitting light from said source, and a terminal mounted on said arm for receiving light from said optical fiber and emitting a ray of light along said arm, a light reflecting mirror disposed in said path of said radiation beam, said mirror being transparent to said radiation and being arranged to receive said light ray emitted from said terminal and to reflect said ray in the direction of said beam toward said part to be inspected, first means for taking an image of the part through which said radiation passes, second means for taking an image of the part sighted by said light ray, wherein said mirror is fixed on a plate, said plate being removably mounted on said arm, and a device for checking horizontality of said arm, said device being mounted on a plate which may be removably fitted on said arm in place of said mirror plate.

* * * * *

UNITED STATES PATENT AND TRADEMARK OFFICE
CERTIFICATE OF CORRECTION

PATENT NO. : 5,177,779
DATED : January 5, 1993
INVENTOR(S) : Michel L. P. Cornu et al.

It is certified that error appears in the above-identified patent and that said Letters Patent is hereby corrected as shown below:

On the title page, Item [75],

The first inventor's name is incorrect, should be,

--Michel L. P. Cornu--

Signed and Sealed this

Twelfth Day of October, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,177,779
DATED : January 5, 1993
INVENTOR(S) : Michel L.P. Cornu et al It is certified that error appears in the above-indentified patent and that said Letters Patent is hereby corrected as shown below:

Column 2, line 8, delete 1;

line 37, change "anticathode" to --anti-cathode-- line 60, change "yy" to --by--

Column 3, line 18, change "a" to --as-- line 48, change "the" to --they--

Signed and Sealed this

Seventh Day of December, 1993

Attest:

BRUCE LEHMAN

Attesting Officer     Commissioner of Patents and Trademarks